United States Patent
Fukuda et al.

(10) Patent No.: US 6,537,553 B1
(45) Date of Patent: Mar. 25, 2003

(54) LEUKOSIALIN: IG FUSION PROTEINS

(75) Inventors: Minoru Fukuda, San Diego, CA (US); Ritsuko Sawada, San Diego, CA (US); Shigeru Tsuboi, San Diego, CA (US)

(73) Assignee: La Jolla Cancer Research Foundation, La Jolla, CA (US)

( * ) Notice: Subject to any disclaimer, the term of this patent is extended or adjusted under 35 U.S.C. 154(b) by 0 days.

(21) Appl. No.: 08/369,754

(22) Filed: Jan. 6, 1995

Related U.S. Application Data (63) Continuation-in-part of application No. 08/073,807, filed on Jun. 8, 1993, now Pat. No. 5,646,248.

(51) Int. Cl.$^7$ ................................................ C12P 21/00

(52) U.S. Cl. .................. 424/192.1; 530/350; 530/387.3; 530/387.5; 530/395; 435/69.7

(58) Field of Search ................................. 530/350, 395, 530/402, 387.3, 387.5; 435/69.1, 69.7; 514/2; 424/192.1

(56) References Cited

FOREIGN PATENT DOCUMENTS

| WO | WO94/00143 | 1/1994 |
|---|---|---|

OTHER PUBLICATIONS

Dwek et al., Science, 269, 1234, 1995.*
Opdenakker, The FASEB Journal, 7, 1330, 1993.*
Levirovitz et al., J. Cell Biology, vol. 121, 449–459, 1993.*
Sueyoshi et al., Bioorg Med. Chem., vol. 2, 1331–8, 1994 (Abstract).*
Bazil et al., Proc. Natl. Acad. Sci, vol. 90, 3792–3796, 1993.*
Scopes, Protein Purification, 132–135, 1982, Springer–Verlag, New York.*
Fukuda, M., "Cell Surface Glycoconjugates as Onco–Differentiation Markers in Hematopoietic Cells", *Biochem. Biophys. Acta*, 780:119–150, (1985).
Fukuda, M. and Fukuda, M.N., in: *Biology of Glycoproteins* (Ivatt, R.J., ed.), pp. 183–234, Plenum Publishing Corp., N.Y. (1984).
Feizi, T., "Demonstration by monoclonal antibodies that carbohydrate structures of glycoproteins and glycolipids are onco–developmental antigens", *Nature*, 314: 53–57, (1985).
Fukuda et al., "Structure of Sialylated Fucosyl Lactosaminoglycan Isolated from Human Granulocytes*" *The Journal of Biological Chemistry*, 259: 10925–10935, (1984).
Lowe et al., "ELAM–1–Dependent Cell Adhesion to Vascular Endothelium Determined by a Transfected Human Fucosyltransferase cDNA" *Cell*, 63: 475–484, (1990).
Phillips et al., "ELAM–1 Mediates Cell Adhesion by Recognition of a Carbohydrate Ligand, Sialyl–Lex" *Science*, 250: 1130–1132, (1990).

Walz et al., "Recognition by ELAM–1 of the Sialyl–Lex Determinant of Myeloid and Tumor Cells", *Science*, 250: 1132–1135, (1990).
Polley et al., "CD62 and endothelial cell–leukocyte adhesion molecule 1 (ELAM–1) recognize the same carbohydrate ligand, sialy–Lewis x" *PNAS USA*, 88: 6224–6228, (1991).
Larson et al., PADGEM–Dependent Adhesion of Platelets to Monocytes and Neutrophils Is Mediated by a Lineage–Specific Carbohydrate, LNF III (CD15), *Cell*, 63: 467–474, (1990).
Berg et al., "A Carbohydrate Domain Common to Both Sialyl Lea and Sialyl Lex Is Recognized by the Endothelial Cell Leukocyte Adhesion Molecule ELAM–1*", *The Journal of Biological Chemistry*, 266: 14869–14872, (1991).
Sawada et al., "E–selectin–dependent Adhesion Efficiency of Colonic Carcinoma Cells Is Increased by Genetic Manipulation of Their Cell Surface Lysosomal Membrane Glycoprotein–1 Expression Levels*", *The Journal of Biological Chemistry*, 268: 12675–12681, (1993).
Carlsson et al., "Isolation and Characterization of Human Lysosomal membrane Glycoproteins, h–lamp–1 and h–lamp–2" *The Journal of Biological Chemistry*, 263: 18911–18919, (1988).

(List continued on next page.)

*Primary Examiner*—Lorraine Spector
*Assistant Examiner*—Eliane Lazar-Wesley (57) ABSTRACT

The present invention provides antagonists to cell adhesion useful in controlling the negative effects of inflammation, and the metastasis of cancer cells. These antagonists are ligands to E-selectin containing the sialyl Le$^x$ structure, including sialyl Le$^x$ glycoproteins, sialyl Le$^x$ glycolipids, and sialyl Le$^x$ oligsaccharides, and other related sialyl Le$^x$-containing molecules capable of inhibiting E-selectin mediated cell adhesion to endothelial cells. The present invention also provides antibodies against sialyl Le$^x$ determinants capable of interrupting E-selectin mediated cell adhesion, which are also considered antagonists according to the present invention. The present invention also provides methods of using the antagonists of the present invention to reduce inflammation, and methods to inhibit the process of metastasis by carcinogenic cells. The present invention also provides nucleic acid molecules encoding the glycoprotein antagonists of the present invention, in particular soluble chimeric leukosialin, and vectors capable of expressing these nucleic acid molecules, as well as cells capable of producing sialyl Le$^x$ positive recombinant glycoproteins. The present invention further provides a method of determining metastatic potential by comparing the efficiency of E-selectin-mediated adhesion of cell samples. In addition the present invention provides a method of producing a preferred antagonist of the present invention, sialyl Le$^x$ positive glycoproteins, in particular, sialy Le$^x$ positive chimeric leukosialin.

3 Claims, 5 Drawing Sheets

OTHER PUBLICATIONS

Carlsson et al., "Assignment of O–Glycan Attachment Sites to the Hingelike Regions of Human Lysosomal Membrane Glycoproteins Lamp–1 and Lamp–2 1", *Archives of Biochemistry and Biophysics*, 304: 65–73, (1993).

Carlsson et al., "Isolation and Characterization of Leukosialin, a Major Sialoglycoprotein on Human Leukocytes*" *The Journal of Biological Chemistry*, 261: 12779–12786, (1986).

Fukuda et al., "Structures of o–Linked Oligosaccharides Isolated from Normal Granulocytes, Chronic Myelogenous Leukemia Cells, and Acute Myelogenous Leukemia Cells*" *The Journal of Biological Chemistry*, 261: 12796–12806, (1986).

Maemura and Fukuda, "Poly–N–acetyllactosaminyl O–Glycans Attached to Leukosialin", *The Journal of Biological Chemistry*, 267: 24379–24386, (1992).

Bierhuizen et al., "Expression cloning of a cDNA encoding UDP–GlcNAc:Galβ1–3–GalNAc–R(GlcNAc to GalNAc) β1–6GlcNAc transferase by gene transfer into CHO cells expressing polyoma large tumor antigen" *PNAS U.S.A.*, 89: 9326–9330, (1992).

Kukowska–Latallo et al., "A cloned human cDNA determines expression of a mouse stage–specific embryonic antigen and the Lewis blood group α(1,3/1,4) fucosyltransferase", *Genes & Development*, 4: 1288–1303, (1990).

Mulligan et al., "Protective Effects of Sialylated Oligosaccharides in Immune Complex–induced Acute Lung Injury", *J. Exp. Med.*, 178: 623–631, (1993).

Cyster et al., "The dimensions of the T lymphocyte glycoprotein leukosialin and identification of linear protein epitopes that can be modified by glycosylation", *The EMBO Journal*, 10: 893–902, (1991).

Smith et al., "Transfer and Expression of a Murine UDP–Gal:β–D–Gal–α1,3–Galactosyltransferase Gene in Tranfected Chinese Hamster Ovary Cells", *The Journal of Biological Chemistry*, 265: 6225–6234, (1990).

Lee et al., "Alteration of Terminal Glycosylation Sequences of N–Linked Oligosaccharides of Chinese Hamster Ovary Cells by Expression of β–Galactoside α 2,6–Sialyltransferase*", *The Journal of Biological Chemistry*, 264: 13848–13855, (1989).

Williams and Fukuda, Accumulation of Membrane Glycoproteins in Lysosomes Requires a Tyrosine Residue at a Particular Position in The Cytoplasmic Tail, *J. Cell Biology*, 111: 955–966, (1990).

Lowe et al., "ELAM–1 Dependent Cell Adhesion to Vascular Endothelium Determined by a Transfected Human Fucosyltransferase cDNA", *Cell*, 63: 475–484, (1990).

Weinstein et al., "Sialylation of glycoprotein Oligosaccharides N–linked to Asparagine", *The Journal of Biological Chemistry*, 257: 13845–13853, (1982).

Lowe et al., "Molecular Cloning of a Human Fucosyltransferase Gene That Determines Expression of the Lewis x and VIM–2 Epitopes but Not ELAM–1–dependent Cell Adhesion*", *The Journal of Biological Chemistry*, 266: 17467–17477, (1991).

Pallant et al., "Characterization of cDNAs encoding human leukosialin and localization of the leukosialin gene to chromosome 16", *PNAS USA*, 86:1328–1332, (1989).

Saitoh et al., "Differential Glycosylation and Cell Surface Expression of Lysosomal membrane Glycoproteins in Sublines of a Human Colon Cancer Exhibiting Distinct Metastatic Potentials*", *The Journal of Biological Chemistry*, 267: 5700–5711, (1992).

Saiki et al., "Primer–Directed Enzymatic Amplification of DNA with a Thermostable DNA Polymerase", *Science*, 239: 487–491, (1988).

Aruffo et al., "CD44 Is the Principal Cell Surface Receptor for Hyaluronate", *Cell*, 61: 1303–1313, (1990).

Takebe et al., "SRα Promoter: an Efficient and Versatile Mammalian cDNA Expression System Composed of the Simian Virus 40 Early Promotor and the R–U5 Segment of Human T–Cell Leukemia Virus Type 1 Long Terminal Repeat", *Mol. Cell. Biol.*, 8: 466–472, (1988).

Weston et al., "Molecular Cloning of a Fourth Member of a Human α(1,3)Fucosyltransferase Gene Family", *The Journal of Biological Chemistry*, 267: 24575–24584, (1992).

Sugden et al., "A Vector that Replicates as a Plasmid and Can Be Efficiently Selected in B–Lymphoblasts Transformed by Epstein–Barr Virus", *Mol. cell. biol.*, 5: 410–413, (1985).

Williams et al., "Embryonic Lethalities and Endothelial Tumors in Chimeric Mice Expressing Polyoma Virus Middle T Oncogene", *Cell*, 52: 121–131, (1988).

Kameyama et al., "Total synthesis of sialyl Lewis X*", *Carbohydrate Res.*, 209: C1–C4, (1991).

Ball and Fanger, "The Expression of Myeloid–Specific Antigens on Myeloid Leukemia Cells: Correlations With Leukemia Subclasses and Implications for Normal Myeloid Differentiation", *Blood*, 61: 456–463, (1983).

Morikawa et al., "In Vivo Selection of Highly Metastatic Cells from Surgical Specimens of Different Primary Human Colon Carcinomas Implanted into Nude Mice", *Cancer Res.*, 48: 1943–1948, (1988).

Lee et al., "Granulocytic Differentiation of HL–60 Cells Is Associated with Increase of Poly–N–acetyllactosamine in Asn–linked Oligosaccharides Attached to Human Lysosomal Membrane Glycoproteins*", *The Journal of Biological Chemistry*, 265: 20476–20487, (1990).

Weller et al., "Cloning of the Mouse Endothelial Selecins", *J. Biol. Chem.*, 267: 15167–15183, (1992).

* cited by examiner

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 24 base pairs
       (B) TYPE: nucleic acid
       (C) STRANDEDNESS: single
       (D) TOPOLOGY: linear     (xi) SEQUENCE DESCRIPTION: SEQ ID NO:1:

TTTGAATTCC TGGAAATGGC CACG                         24

(2) INFORMATION FOR SEQ ID NO:2:

(i) SEQUENCE CHARACTERISTICS:
       (A) LENGTH: 26 base pairs
       (B) TYPE: nucleic acid
       (C) STRANDEDNESS: single
       (D) TOPOLOGY: linear     (xi) SEQUENCE DESCRIPTION: SEQ ID NO:2:

AAAAGATCTG AGTTCTCATC TGGGTT                       26

LEUKOSIALIN: IG FUSION PROTEINS

This application is a continuation-in-part of U.S. application Ser. No. 08/073,807, filed Jun. 8, 1993, which issued as U.S. Pat. No. 5,646,248 on Jul. 8, 1997, and which is herein incorporated by reference in its entirety.

Throughout this application, various publications are referred to more fully disclose the state of the art. These references are hereby incorporated by reference.

This invention was made in part with Government support under Grant Nos. CA 48737 and CA 33895 awarded by the National Institute of Health. The Government may have certain rights in the invention.

BACKGROUND OF THE INVENTION

Cells recruited to a site of inflammation represent pivotal components of the human inflammatory response. These cells include a large array of immune cells which may exert a beneficial effect due to their combined ability to combat infection and promote the restoration of normal tissue integrity. However, these immune cells may also contribute to undesirable effects such as tissue damage arising from autoimmune diseases or as a consequence of excessive cell recruitment.

The pathological consequences of inflammation are largely mediated by immune cells such as neutrophils and monocytes, and the molecules they elaborate. These circulating cells must first exit the circulatory system in order to participate in the inflammatory processes at extravascular locations. Initial events in this process involve adhesion between myeloid cells and vascular endothelial cells. During inflammation, endothelial cells are activated by cytokines, resulting in the expression of E-selectin on the endothelial cell surfaces. Consequently, leukocytes are slowed down through the interaction of their cell surface carbohydrates with E-selectin, a process referred to as "rolling". This interaction results in the capturing of chemoattractants by leukocytes and the activation of integrins in granualocytes and monocytes, resulting in a stronger adhesion of the leukocytes to endothelial cells and extravasation of leukocytes.

E-selectin is a selectin that is transiently expressed on endothelial cells 2 to 8 hours after stimulation of IL-1 and other inflammatory agents, and mediates a neutrophil adhesion pathway distinct from that mediated by ICAMS and leukocyte integrins. The neutrophil chemoattractant IL-8, which is secreted by activated endothelial cells, acts on neutrophils as a feedback inhibitor to attenuate the hyperadhesive interaction between neutrophils and E-selectin receptors. P-selectin is located in a-granules of platelets and Weibel-Palade bodies of endothelial cells, and is rapidly mobilized to the surface of these cells after stimulation by products of the clotting cascade such as thrombin, where it mediates adhesion of neutrophils and monocytes. Selectins function in a wide range of cell interactions in the vasculature and are expressed both on leukocytes and endothelial cells. Selectins mediate adhesion events within the blood vascular compartment through calcium-dependent recognition of specific carbohydrates.

Tumor metastasis resembles the inflammation process. During metastasis tumor cells adhere to endothelial cells and then extravasculate from the blood stream into the surrounding tissue. In addition, it has been shown that the amount of sialyl Le$^x$ and sialyl Le$^a$ structures are increased in carcinoma cells and that some tumor cells can adhere to endothelial cells by selectin-mediated interactions. Since metastasis is the major cause of death for cancer patients, there is a need to control the process of metastasis.

The present invention provides a means for controlling both the adverse effects of the inflammatory response and the spread of tumor metastasis, and provides related advantages as well.

SUMMARY OF THE INVENTION

The present invention provides antagonists to cell adhesion which are useful in controlling the negative effects of inflammation, and the metastasis of cancer cells. These antagonists are molecules capable of mediating cell adhesion to endothelial cells. The antagonists are ligands to E-selectin containing the sialyl Le$^x$ structure, and antibodies to sialyl Le$^x$-determinants. Ligands to E-selectin according to the present invention are sialyl Le$^x$-containing molecules such as sialyl Le$^x$ glycoproteins, sialyl Le$^x$ glycolipids, and sialyl Le$^x$ oligosaccharides, and other related sialyl Le$^x$-containing molecules capable of inhibiting E-selectin mediated cell adhesion to endothelial cells.

The present invention also provides methods of using the antagonists of the present invention to reduce inflammation, and methods to inhibit the process of metastasis by carcinogenic cells. The present invention also provides nucleic acid molecules encoding soluble glycoprotein antagonists, in particular nucleic acid sequences encoding soluble leukosialin, and vectors and cells capable of expressing soluble sialyl Le$^x$ containing antagonists. The present invention further provides a method of determining metastatic potential by comparing the efficiency of E-selectin-mediated adhesion of the cells to be tested. In addition the present invention provides a method of producing a preferred antagonist of the present invention, soluble sialyl Le$^x$ positive glycoproteins, in particular soluble chimeric sialyl Le$^x$ positive leukosialin.

BRIEF DESCRIPTION OF THE FIGURES

FIG. 3 parts A–D show the adhesion of various colonic carcinoma cells to mouse endothelial cells derived from brain, bEnd-4 (FIG. 3A), from mid gestation chimeric embryos (FIG. 3B), from skin (FIG. 3C), and from thymus (FIG. 3D).

FIG. 5 parts A–C shows the inhibition of cell adhesion to mouse endothelial cells by soluble lamp-1 (FIG. 5A), soluble leukosialin (FIG. 5B) and anti-sialyl Le$^x$ antibody (FIG. 5C).

DETAILED DESCRIPTION OF THE INVENTION

The present invention provides antagonists to cell adhesion which are useful in controlling the negative effects of inflammation, and in preventing cell adhesion during the process of metastasis of cancer cells. These antagonists are molecules containing sialyl Le$^x$ termini which inhibit E-selectin mediated cell adhesion to endothelial cells, or anti-sialyl Le$^x$ antibodies capable of inhibiting E-selectin mediated cell adhesion.

The present invention is based on studies demonstrating that E-selectin dependent adhesion of carcinoma cells to endothelial cells is effectively inhibited by the molecules containing sialyl Le$^x$ termini, as well as anti-sialyl Le$^x$ antibodies. These studies provide evidence that E-selectin mediated adhesion of tumor cells to endothelial cells is a critical factor in tumor metastasis.

Polylactosaminoglycans are high molecular weight carbohydrates bound to proteins and lipids. Polylactoaminoglycans are composed of repeating units of N-acetyllactosamine, (Galβ1→4GlcNAcβ1→3)$_n$. These polylactoaminoglycans are often modified resulting in determinants characteristic for different cell types and stages of differentiation (Fukuda, M., *Biochem. Biophys. Acta* 780:119–150 (1985), Fukuda, M. and Fukuda, M. N. *Biology of Glycoproteins* (Ivatt, R. J., ed), pp. 183–234, Plenum Publishing Corp., N.Y. (1984), Feizi, T., *Nature* 314:53–57 (1985)). For example, the polylactosaminoglycans of granulocytes and monocytes are enriched for the terminal structures Le$^x$ (Galβ1→4(Fucα1→3)GlcNAcβ→R), or sialyl Le$^x$ (NeuNAcα 2→3Galβ1→4 (Fucα1→3)GlcNAcβ1→R) (Fukuda et al., *J. Biol. Chem.* 259:10925–10935 (1984)). It has recently been discovered that the sialyl Le$^x$ structures in these leukocytes serve as ligands for selectins present on endothelial cells (E-selectin) and platelets (P-selectin) (Lowe et al., *Cell* 163:475–484 (1990); Phillips et al., *Science* 250:1130–1132 (1990); Walz et al. *Science* 250:1132–1135 (1990); Polley et al *PNAS USA* 88:6224–6228 (1991); Larsen et al. *Cell* 63:467–474 (1990)). It has also been demonstrated that an isomer of sialyl Le$^x$, sialy Le$^a$, NeuNAcα2→3Galβ1→3(Fucα1→4)GlcNacβ→R, also may serve as a ligand for E-selectin (Berg et al., *J. Biol. Chem.* 266:14869–14972 (1991)).

Sialyl Le$^x$ termini can be naturally occurring in both N-glycans and O-glycans. Lamp-1 (lysosomal membrane glycoproteins-1, as described in Sawada et al., *J. Biol. Chem.* 268:12675–12681 (1993), for example) contains 18 N-glycans and five O-glycans (Carlsson et al. *J. Biol. Chem.* 263:18911–18919 (1988), Carlsson et al., *Arch. Biochem. Biophys.* 304:65–73 (1993)), while leukosialin contains more than 70 O-glycans and one N-glycan (Carlsson et al. *J. Biol. Chem.* 261:12779–12786 (1986). It has been shown that sialyl Le$^x$ formation in O-glycans is dependent on the core 2 branch, Galβ1→4GlcNAcβ1→6GalNAc (Fukuda et al., *J. Biol.Chem.* 261:12796–12806 (1986), Maemura et al., *J. Biol. Chem.* 267:24379–24386 (1986)). Therefore, in order to recombinantly produce a soluble leukosialin containing an effective number of sialyl Le$^x$ termini, cell lines stably transfected with both cDNA encoding core 2 β-1,6-N-acetylglucosaminyltransferase (Bierhuizen et al., *Proc. Natl. Acad. Sci. U.S.A.* 89:9326–9330 (1990)) and cDNA encoding Fuc-TIII (Kukowska-Latallo et al., *Genes & Devel* 4:1288–1303 (1990) were used.

As shown in the Examples below, adhesion of human colonic carcinoma cells to various endothelial cells is inhibited by sialyl Le$^x$-containing molecules including sialyl Le$^x$-glycolipids, and sialyl Le$^x$-containing soluble glycoproteins such as soluble leukosialin, and lamp-1. In addition anti-sialyl Le$^x$ antibodies inhibit E-selectin mediated adhesion.

Accordingly, the present invention provides sialyl Le$^x$ containing antagonists capable of interfering with E-selectin mediated cell adhesion. Preferred embodiments of the antagonists of the present invention are recombinantly produced glycoproteins carrying the sialyl Le$^x$ determinant. These glycoproteins function in an efficient manner as therapeutic molecules by virtue of their ability to effectively present the sialyl Le$^x$ determinants to vascular selectins thus blocking neutrophil/monocyte-selectin interactions in inflammation, for example. It is expected that glycoproteins will have serum half-lives considerably longer than a lower molecular weight sialyl Le$^x$ tetrasaccharide, for example. In addition, the larger molecule is thought to present the sialyl Le$^x$ determinant in a manner more favorable to efficient binding interaction than a smaller molecule such as the isolated tetrasaccharide. This is consistent with evidence that glycopeptides are more efficient than oligosaccharides in the rat injury model, described, for example, in Mulligan et al., *J. Exp. Med.* 178:623–631 (1993).

A preferred embodiment of the antagonists of the present invention is a Le$^x$ positive leukosialin molecule. This molecule is preferably a soluble chimeric leukosialin protein which can be expressed recombinantly in appropriate cell lines. Leukosialin is a major surface-located glyprotein on human leukocytes which contains a high percentage of O-glycans, and displays the sialyl Le$^x$ determinant on some leukocytes, and maintains an extended linear conformation suitable for oligosaccharide presentation (Cyster et al. *EMBO J* 10:893–902 (1991)).

In order to produce recombinant glycoproteins which express the sialyl Le$^x$ determinant, cell lines such as Chinese hamster ovary cells (CHO cells), which express the necessary additional enzymes, are utilized in which the glycosylation phenotype has been altered by stable introduction of fucosyltransferase genes such as human Fuc-TIII, Fuc-TV, Fuc-TVI, and Fuc-TVII genes so as to render them competent to construct the sialyl Le$^x$ determinants. The CHO cell line is particularly appropriate because the glycan, molecules constructed by these cells are well-defined (Smith et al., *J. Biol. Chem.* 265:6225–6234 (1990), Lee et al., *J. Biol. Chem.* 264:13848–13855 (1989), contain other necessary glycosyltransferases and other enzymes, and mirror aspects of the glycans constructed by blood cells.

One such recombinant glycoprotein is soluble chimeric leukosialin-IgG, as described in Example I below. Soluble leukosialin is advantageously expressed as a chimeric protein such as leukosialin-IgG for ease in purification.

Figure 1:
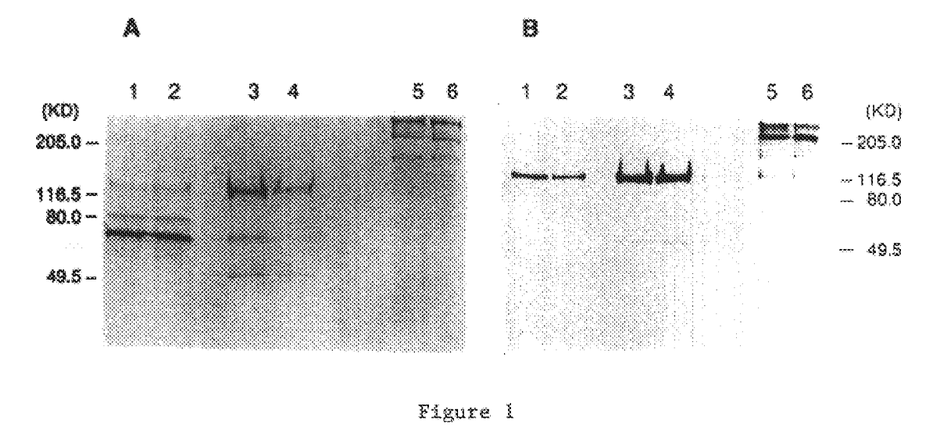
FIGS. 1A & 1B show the purification of soluble leukosialin generated from control CHO cells and CHO cells expressing sialyl Le$^x$-structures.

The present invention also provides a method of producing a soluble sialyl Le$^x$ positive glycoprotein antagonist of the present invention. The soluble sialyl Le$^x$ positive glycoprotein is recombinantly produced in appropriate cell lines containing both a vector capable of expressing a soluble form of the glycoprotein, and a vector which expresses a fucosyltransferase enzyme which directs the production of sialyl Le$^x$ structures, as well as additional necessary enzymes. Soluble leukosialin, for example, is prepared from cell lines such as CHO cells stably transfected with a vector that directs the expression of a soluble form of leukosialin and with a vector encoding an appropriate fucosyltransferase enzyme such as Fuc-TIII. These cells are stably transfected with a cDNA encoding core 2 β-1,6-N-acetylglucosaminyltransferase as described in Example I below, and express all additional necessary enzymes as set forth below in the definition of sialy Le$^x$, as well as being transfected with vectors expressing the glycoprotein and a fucosyltransferase enzyme which directs the production of sialyl Le$^x$ structures. The transfected cells were confirmed to express sialyl Le$^x$ determinants by immunofluorescence as described in Williams and Fukuda, *J. Cell. Biol.* 111:955–966 (1990). In order to efficiently purify the soluble leukosialin, the cDNA sequence for leukosialin was fused with the sequence for the IgG constant and hinge region. The resultant protein was then purified from the conditioned media of the cell culture. The chimeric protein is characterized in Example I, FIG. 1 as shown below. This protein has a $M_r$ of approximately 120,000, as shown in FIG. 1.

Figure 5:
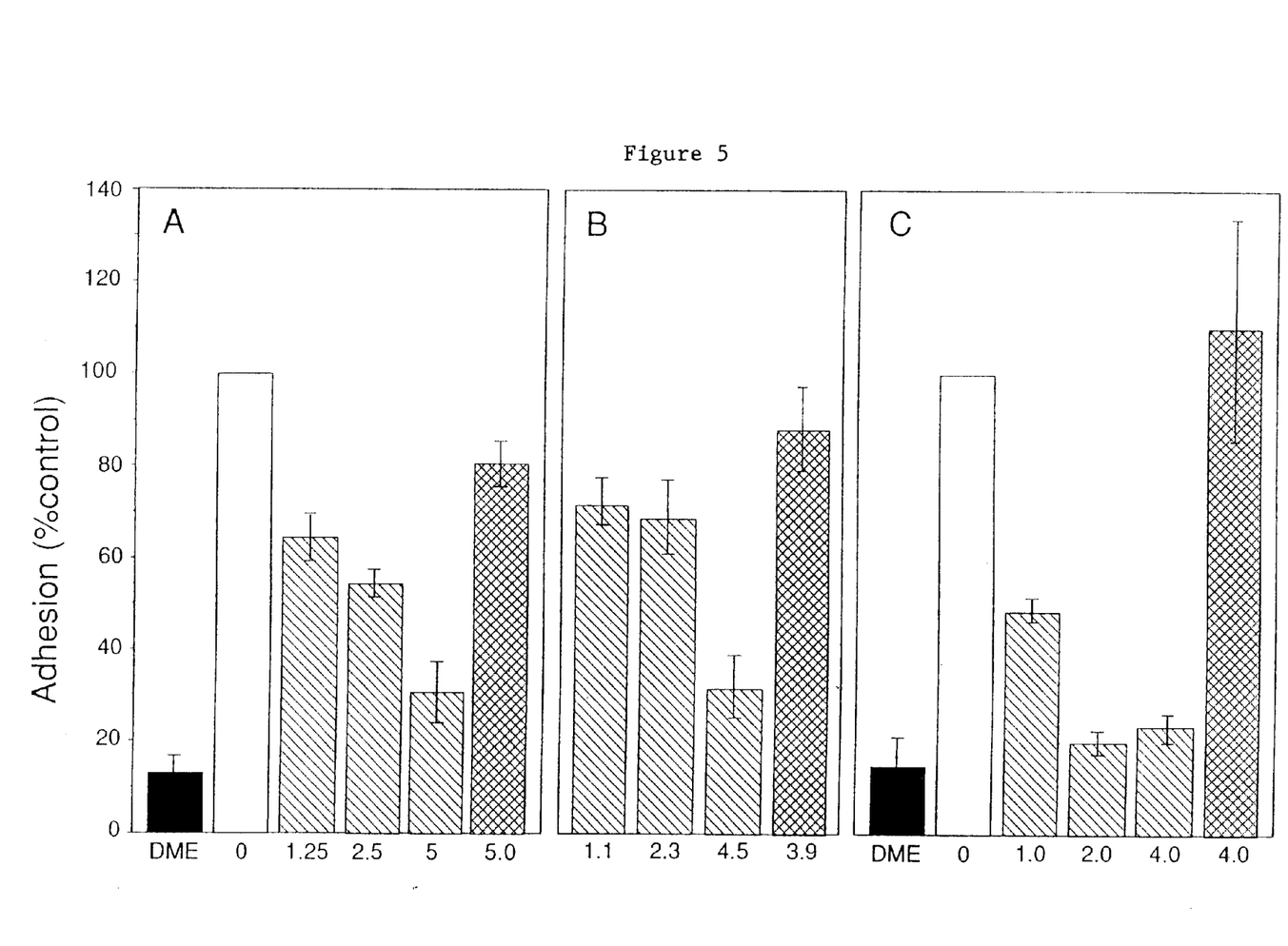

A soluble leukosialin lacking the sialyl $Le^x$ determinants was similarly prepared from the conditioned media of CHO cells, except that a control cell line was used which was stably transfected only with the vector encoding the soluble leukosialin chimeric protein, and not a vector encoding Fuc-TIII. When the soluble leukosialins were tested in an adhesion assay described in Example V (FIG. 5), sialyl $Le^x$ positive leukosialin inhibited the adhesion of SM cells to mouse tEnd.1 cells in a concentration dependent manner, whereas the soluble sialyl $Le^x$ negative leukosialin inhibited binding only minimally.

Figure 4:
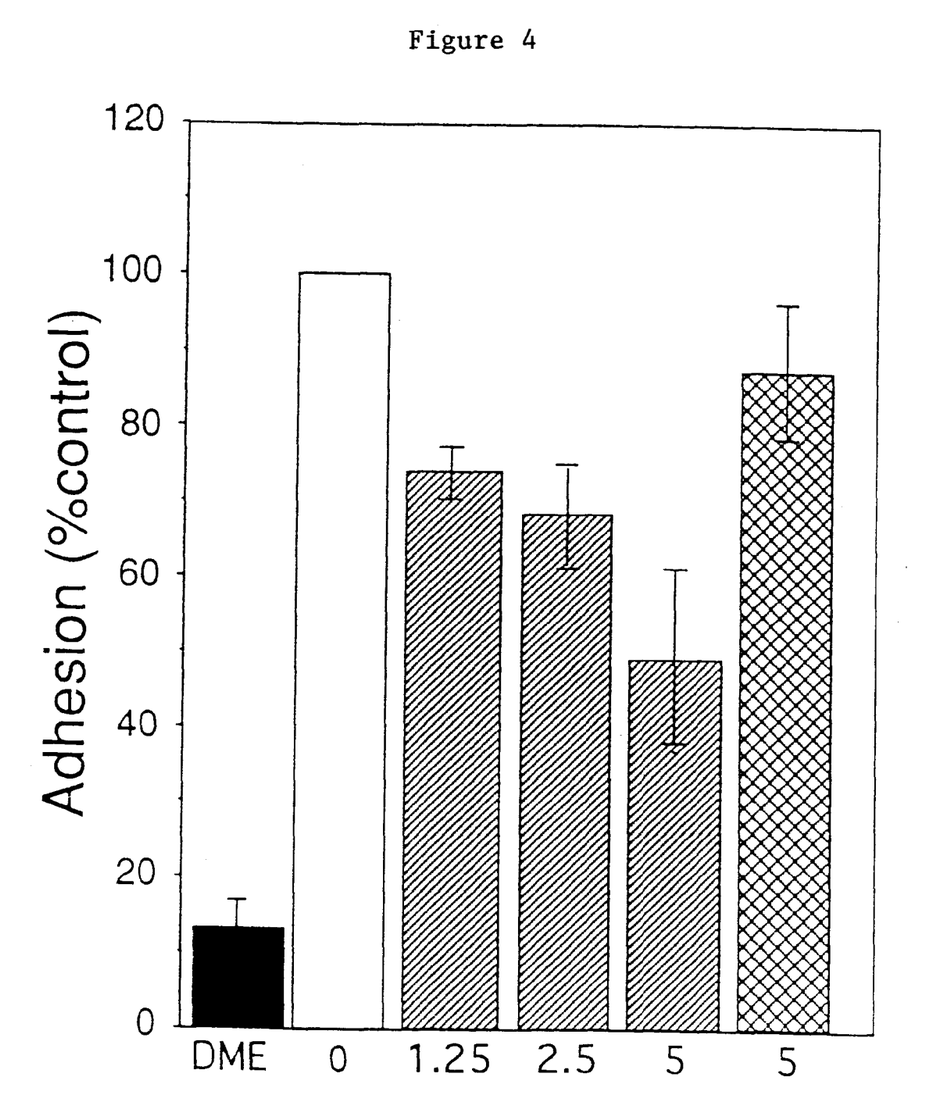
FIG. 4 shows the inhibition of adhesion to mouse endothelial cells by sialyl Le$^x$-glycolipid.

Similarly, a soluble lamp-1 protein was prepared from a cell line stably transfected with a vector that directs the expression of a soluble form of lamp-1 and with a vector that encodes a human α-1,3/4 fucosyltransferase (Fuc-T III) capable of creating the sialyl-$Le^x$ determinant using CHO cell oligosaccharide precursors (Lowe et al., *Cell* 63:475–484 (1990)). This soluble lamp-1 containing the sialyl $Le^x$ was also able to inhibit the adhesion of SM cells to activated mouse tEnd.1 cells as shown in FIG. 4.

As demonstrated in the Examples provided below, adhesion of human colonic carcinoma cells to activated human endothelial cells, E-selectin expressing CHO cells, and activated mouse endothelial cells is similar. Adhesion of human carcinoma cells to mouse endothelial cells is similar to adhesion of the same cells to human endothelial cells, and also appears to be mediated by E-selectin. Therefore, the mouse system is useful for studies of tumor metastasis at the level of E-selectin dependent adhesion of carcinoma cells. The sialyl $Le^x$ containing glycoprotein and glycolipid antagonists are equally effective against the various E-selectin expressing cells, with the exception that inhibition of adhesion by sialyl $Le^x$ glycolipid to mouse cells is not as effective as the inhibition of the same carcinoma cells to human endothelial cells under the same conditions.

In another aspect of the invention, it has now been established that the efficiency of E-selectin-dependent adhesion of various carcinoma cells correlates with the metastatic potential of the cell. High metastatic carcinoma cells adhere more strongly to E-selectin-expressing cells than the corresponding low metastatic carcinoma cells. The correlation of E-selectin-dependent adhesion with the metastatic potential is demonstrated in the Examples below.

Therefore, the present invention provides methods of assessing the metastatic potential of a cell sample according to the adhesion assays provided in the Examples below. Metastatic potential refers to the degree to which a cell type metastasizes in various tissues. Such adhesion assays can take the form of testing for percentage of cells bound, for example, as described in Examples II and III. The assay shown in FIG. 3, for example, correlates with the degree of metastatic potential already established for the colonic carcinoma cells used in this assay. Alternatively such assays could be performed by determining the quantity of an appropriate antagonist needed to inhibit the adhesion of the cells to endothelial cells. For example, as described below in Example V, FIG. 5, demonstrates the inhibition of cell adhesion to mouse endothelial cells by antagonists containing sialyl $Le^x$ structures such as soluble leukosialin, soluble lamp-1, as well as anti-sialyl $Le^x$ antibodies. Various cell systems can be used for such assays. It is shown in the Examples below that activated human endothelial cells, E-selectin-expressing cells such as CHO cells, and activated mouse endothelial cells are equally effective as assay systems.

The present invention also provides antibodies to the sialyl $Le^x$ determinants. These antibodies are capable of interrupting E-selectin mediated binding, as shown in the Examples below, and are considered antagonists according to the present invention. These antibodies can be made by methods conventional in the art. For examples, polyclonal antiserum can be raised in appropriate animals, such as rabbits, mice or rats. Purified sialyl $Le^x$ tetrasaccharides, or antigenically reactive molecules containing the sialyl $Le^x$ determinants, can be used to immunize the animal by methods known to those in the art. Serum samples are collected until the titer is appropriate. Various fractions of the antisera, such as IgG, can be isolated by means well known in the art. Alternatively, anti-sialyl $Le^x$-immunogens can be used to obtain monoclonal antibodies, by means well known in the art, as described, for example in Harlow and Lane, *Antibodies: A Laboratory Manual* (Cold Springs Harbor Laboratory, 1988), herein incorporated by reference. Altered antibodies such as chimeric, humanized, CDR-grafted or bifunctional antibodies can also be produced by methods well known in the art. Such antibodies can also be produced by hybridoma, chemical synthesis or recombinant methods described, for example, in Sambrook et al., *Molecular Cloning: A Laboratory Manual* 2d ed. (Cold Spring Harbor Laboratory 1989), herein incorporated by reference. The antibodies can be used for determining the presence or purification of the soluble chimeric leukosialin of the present invention. With respect to the detection of such polypeptides, the antibodies can be used for in vitro diagnostic or in vivo imaging methods.

As used herein, the term "sialy $Le^x$ termini", "sialy $Le^x$ determinant" or "$Le^x$ positive" refers to a class of oligosaccharide determinants represented by sialyl Lewis x, or NeuNAcα 2→3Galβ1→4(Fucα1→3)GlcNAcβ1→R, where R is a glycan. The synthesis of these molecules is catalyzed by glycosyltransferase enzymes. Biosynthetically sialyl Lewis$^x$ molecules such as the type II-based sialyl $Le^x$ molecule (where R=glycoprotein or glycolipid moieties that may contain one or more additional lactosamines (Galβ1, 4GlcNAcβ1, 3 repeat units)) are constructed using oligosaccharide precursors whose terminal galactose residues are substituted with α(2,3)-linked sialic acid via the action of an α(2,3)sialyltransferase (Weinstein et al. *J. Biol. Chem.* 257:13845–13853 (1982)). The terminal GlcNac residues on this sialylated precursor molecule, or on its neutral predecessor, are then substituted with α(1,3)-linked fucose residues via the action of an α(1,3) fucosyltransferase to form sialyl $Le^x$ residues. The recombinant production of sialyl $Le^x$ molecules is accomplished by the transfection of cell lines such as Chinese hamster ovary (CHO) cell lines with human α(1,3) glycosyltransferase (Lowe et al., *Cell* 63:475–484 (1990), Lowe et al., *J.Biol.Chem.* 266:17467–17478 (1991)), as well with nucleic acid encoding the molecule to be produced. Production of sialyl $Le^x$ positive molecules such as sialyl $Le^x$ positive chimeric leukosialin and slalyl $Le^x$ positive lamp-1 is described in the Examples below.

As used herein, the term "sialy $Le^a$ termini" or "$Le^a$ determinant" refers to an isomer of sialyl $Le^x$ molecule, which are constructed from sialylated type I precursors by the action of α(1,4) fucosyltransferases similarly to the pathway describe for sialy $Le^x$ structures as described above (NeuNAcα2→3Galβ1→3(Fucα1→4)GlcNAcβ1→R, where R is a glycan).

As used herein the term "leukosialin" refers to a major sialylglycoprotein on the surface of leukocytes (Maemura, K. and Fukuda, M., *J. Biol. Chem.* 267:24379–24366

(1992), Pallant et al. *PNAS USA* 86:1328–1332 (1989)). Leukosialin is considered to be closely related to or identical to the sialophorin molecule, which is involved in T-cell proliferation (Pallant et al., supra, 1989). Leukosialin contains approximately 80 O-glycans and one N-glycan per molecule. Leukosialin may be isolated by immunoprecipitation and fractionation, according to the procedure described in Maemura et al., supra (1992). The isolation of cDNAs encoding human leukosialin is described in Pallant et al. *PNAS USA* 86: 1328–1332 (1988). The recombinant production of soluble leukosialin using a cDNA encoding leukosialin is described below in Example I.

As used herein, the terms "lamp-1" and "lamp-2" refers to lysosomal membrane glycoproteins 1 and 2 respectively, the most abundant glycoproteins within the lysosomal membrane, which are described, for example, in Saitoh et al., *J. Biol. Chem.* 267:5700–5711 (1992), Sawada et al., *J. Biol. Chem.* 268:12675–12681 (1993), and application Ser. No. 08/073,807, which are herein incorporated by reference.

As used herein the term "glycolipid" refers to a hybrid molecule containing both carbohydrate and lipid groups attached covalently or through weak bonding, as described, for example, in Fukuda, M., *Biochem. Biophys. Acta* 780:119–150 (1985). The preparation of a synthetic glycolipid according to the present invention is described in Phillips et al., *Science* 250:113–1132 (1990).

As used herein the term "glycoprotein" refers to the class of conjugated proteins containing carbohydrate groups attached covalently to the polypeptide chain, as described, for example, in Fukuda, M., supra (1985).

As used herein the term "soluble" polypeptide such as soluble leukosialin refers to a non-naturally occurring cleaved polypeptide which is normally membrane-bound, and which now functions as a secreted molecule while retaining the ability to bind to molecules and is recognized by its membrane-bound counterpart, for example, cell surface selectins. As used herein the term "leukosialin-derived polypeptide" refers to a soluble, biologically active fragment of human leukosialin expressed by its respective nucleic acid. As used herein the term "active fragment" or "biologically active fragment" of the sialylglycoproteins of the present invention refers to any portion of a sialylglycoprotein which contains the ligand portion recognized by molecules such as selectins to which the intact sialylglycoprotein binds. Methods of determining the ability to bind to selectins are well known to those of skill in the art and are set forth below.

As used herein the term "chimeric glycoprotein" such as "chimeric leukosialin" refers to a protein produced recombinantly by a vector containing nucleic acid encoding the glycoprotein, or a biologically active portion thereof, fused to nucleic acid encoding a second protein, or a portion of a second protein, which is expressed as a fused protein. The chimeric protein contains the same amino acid sequence as found in the original proteins or fragments thereof. For example, Example I below describes the production of a soluble leukosialin-IgG chimera from a vector containing a cDNA sequence encoding soluble leukosialin fused to a sequence encoding human IgG1 hinge plus constant region ligated to yield the vector pSRαs-leu-IgG. When expressed in an appropriate cell line the chimeric leukosialin-IgG protein is produced.

As used herein, the term "metastatic potential" refers the tendency of tumor cells or a tumor cell line to metastasize into other organs as determined by the colonization of tumor cells at a site distant from the original site of the tumor cells.

As used herein, the term "purified" means that the molecule or compound is substantially free of contaminants normally associated with a native or natural environment. The methods available for the purification of a soluble proteins include precipitation, gel filtration, ion-exchange, reverse-phase and affinity. chromatography. Other well-known methods are described in Deutscher et al., *Guide to Protein Purification: Methods in Enzymology* Vol. 182, (Academic Press 1990), which is incorporated herein by reference.

The present invention also provides isolated nucleic acids which encode the amino acid sequences corresponding to the peptide or polypeptide portion of the glycoprotein antagonists of the present invention. Examples of such nucleic acids include, but are not limited to, the nucleic acids encoding chimeric leukosialin molecules, such as is described in Example I below. The invention also encompasses "equivalent nucleic acids" to the nucleic acid molecules encoding the polypeptide portion of the sialylglycoproteins of the present invention wherein the equivalent nucleic acids are characterized by changes in non-coding regions that do not alter the phenotype of the polypeptides produced therefrom. As used herein, the term "nucleic acid" encompasses RNA as well as single and double-stranded DNA and cDNA. As used herein the term "polypeptide" encompasses any naturally occurring allelic variant thereof as well as any recombinant form.

The present invention also provides a vector capable of directing the expression of an isolated nucleic acid molecule such as DNA, cDNA or RNA encoding the polypeptide portions of the glycoprotein antagonists of the present invention. In particular, the present invention provides a vector capable of directing the expression of soluble chimeric leukosialin. Examples of such vectors are viruses, such as bacteriophages, baculoviruses and retroviruses; cosmids, plasmids and other recombinant vectors. Nucleic acid molecules are inserted into vector genomes by methods well known in the art. For example, insert and vector DNA can both or individually be exposed to restriction enzymes to create complementary ends on both molecules that base pair with each other and which are then joined together with a ligase. Alternatively, synthetic nucleic acid linkers can be ligated to the insert DNA that correspond to a restriction site in the vector. The vector is then digested with the respective restriction enzyme and the respective nucleic acid may then be inserted. Additionally, an oligonucleotide containing a termination codon and an appropriate restriction site can be ligated into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 promoters for in vitro transcription of sense and anti-sense RNA. Other means are available.

Also provided are vectors containing a DNA molecule encoding a glycoprotein antagonist, in particular, a soluble chimeric leukosialin, adapted for expression in a bacterial cell, a yeast cell, a mammalian cell and other animal cells. The vectors additionally comprise the regulatory elements necessary for expression of the DNA in the bacterial, yeast, mammalian or animal cells so located relative to the DNA encoding soluble leukosialin-derived polypeptide as to permit expression thereof. Regulatory elements required for 
expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Sambrook et al., *Molecular Cloning: A Laboratory Manual* 2d ed. (Cold Spring Harbor Laboratory 1989)). Similarly a eucaryotic expression vector includes a heterologous or homologous promoter for RNA polymerase II, a downstream polyadenylation signal, the start codon AUG, and a termination codon for detachment of the ribosome. Such vectors can be obtained commercially or assembled by methods well known in the art, for example, the methods described above for constructing vectors in general. Expression vectors are useful to produce cells that express the polypeptide.

This invention provides an appropriate mammalian cell containing both a vector that directs the expression of a soluble glycoprotein antagonist of the present invention, and a vector that directs the expression of fucosyltransferases such as Fuc-TIII, which directs sialyl Le$^x$ formation in conjunction with α-2,3-sialyltransferase. As used herein, the term "appropriate mammalian cell" refers to a mammalian cell which expresses all of the necessary enzymes to produce sialyl Le$^x$ structures on the soluble glycoprotein, either naturally or by stable transfection. For example, appropriate mammalian cells must be α-2,3-sialyltransferase positive. As described above, this insures the production of a soluble glycoprotein expressing sufficient sialyl $Le^x$ termini to be an effective antagonist to E-selectin mediated adhesion according to the present invention. An example of a appropriate mammalian cell according to the present invention is the CHO cell line described in Example I below, used for expressing sialyl $Le^x$ positive chimeric leukosialin. Various other mammalian cells which may be utilized as hosts, include, for example, CHO cells, as described below, in addition to mouse fibroblast cell NIH3T3, HeLa cells and Ltk− cells. Expression plasmids such as those described supra can be used to transfect mammalian cells by methods well known in the art such as calcium phosphate precipitation, DEAE-dextran, electroporation, microinjection or lipofection.

The present invention also provides a composition of one or more of the antagonists of the present invention in addition to a carrier wherein the concentration of the antagonists is sufficient to inhibit a selectin as described in the Examples below. In particular, the present invention provides a pharmaceutical composition containing a pharmaceutical carrier and any of the purified sialyl $Le^x$ containing molecules including sialyl $Le^x$ positive glycoproteins or active fragments thereof, glycolipids, oligosaccharides, or other molecules containing sialyl $Le^x$ termini, either alone or in combination with each other. Particularly preferred are soluble sialyl $Le^x$ positive glycoproteins such as the chimeric soluble $Le^x$ positive leukosialin described below. These molecules can be recombinantly derived, chemically synthesized or purified from native sources. As used herein, the term "pharmaceutically acceptable carrier" encompasses any of the standard pharmaceutical carriers, such as phosphate buffered saline solution, water and emulsions such as an oil/water or water/oil emulsion, and various; types of wetting agents.

This invention provides a method of modifying a biological function mediated by the regulatory activity of E-selectin by contacting a suitable sample of cells expressing E-selectin with an effective amount of a biologically active antagonist or composition described above. As used herein "an effective amount" refers to an amount of antagonist or mixture of antagonists sufficient to bind to a selectin and thereby prevent or inhibit its regulatory activity. This method is especially useful for modifying the regulatory activity of E-selectin on activated endothelial cells. In particular, the present invention provides a method of reducing the negative effects of inflammation by administering the antagonists of the present invention. In addition, the present invention provides a method of reducing or inhibiting the metastatic spread of cancer cells by administering the antagonists of the present invention. These methods can be practiced in vitro, ex vivo or in vivo.

Methods of administration are well known to those of skill in the art and include, but are not limited to, administration orally, intravenously or parenterally. Administration will be in such a dosage that the adverse effects of inflammation or the metastatic spread of tumor cells is effectively modified. Administration can be effected continuously or intermittently such that this amount is effective for its intended purpose.

The following examples are intended to illustrate but not limit the invention.

EXAMPLE I

Preparation of Chimeric Leukosialin-IgG

A. PLASMID PREPARATION

A cDNA encoding soluble leukosialin was amplified by PCR (Saiki et al., *Science* 239:486–491 (1988)) using PEER3 leukosialin cDNA (Pallant et al., *PNAS USA* 86:1328–1332 (1989) as a template. The 5'-primer sequence for PCR, 5'-TTTGAATTCCTGGAAATGGCCACG-3' (Seq ID No. 1) starts at 7 base pairs upstream from the start codon for leukosialin (Pallant et al., supra) and contains in addition an EcoRI restriction site. Similarly, the 3'-primer sequence, 5'-AAAAGATCTGAGTTCTCATCTGGGTT-3' (Seq ID No. 2) contains a leukosialin sequence in anti-sense from codons 247 to 252 and additional BglII site and AAA at the 5'-end. The amplified leukosialin cDNA was digested with EcoRI and EglII and then purified by agarose gel electrophoresis. In parallel, BamHI and XbaI fragments containing DNA encoding the human IgG1 hinge plus constant region were isolated from pcDM8-CD4/IgG (Aruffo et al., *Cell* 61:1303–1313 (1990)). The EcoRI-BglII fragment of soluble leukosialin CDNA and the BamHI-XbaI fragment of the human IgG1 hinge plus constant region were then ligated into EcoRI and XbaI ends of pSRα (Takebe et al., *Mol. Cell. Biol.* 8:466–472 (1988)) to yield pSRα.s-leu.IgG. CDM8 harboring the chimeric CD4-IgG1 hinge constant region sequence (Aruffo et al., supra) was kindly provided by Dr. Brian Seed at the Massachusetts General Hospital, Boston, Mass.

B. EXPRESSION OF SOLUBLE LEUKOSIALIN IN CHO CELLS

A CHO cell line stably expressing core 2β-1,6-N-acetylglucosaminyltransferase and the membrane form of human leukosialin, CHO-leu.C2GnT, was transfected with pSRα.s-leu.IgG and $pSV_2dhfr$ using lipofectin under similar conditions as described in Bierhuizen and Fukuda, *PNAS USA* 84:9326–9330 (1992). After the transfection, cells were cultured in α-MEM without nucleotides for 14 days. The cells were then propagated with increasing concentrations of methotrexate (Sigma, final concentration of 0.5 μM), and clonal cell lines were obtained by limiting dilution. The supernatant of each clone was tested by immunoblotting for the presence of the leukosialin-IgG chimera using goat anti-human IgG-peroxidase conjugate (Sigma). The cell line expressing the highest amount of soluble leukosialin-IgG chimera was chosen for the next transfection. CHO-leu.C2GnT was prepared and kindly provided by Dr. Marti Bierhuizen at this institute.

A clonal cell line stably expressing soluble leukosialin was then transfected by lipofectin procedure with pcDNAI-Fuc.TIII (Kukowska-Latallo et al., Genes & Dev. 4:1288–1303 (1990); Weston et al., J. Biol. Chem. 267:24575–24584 (1992)) and pHyg (Sugden et al., Mol. Cell. Biol. 5:410–413 (1985)) in a 10:1 molar ratio. The transfected cells were selected in the presence of 400 µg of hygromycin (Sigma) and clonal cell lines were obtained by limiting dilution. Each cell line was assessed for expression of sialyl Le$^x$ by immunofluorescence, as described in Sawada et al., J. Biol. Chem. 268:12675–12681 (1993). A cell line expressing both soluble leukosialin as well as sialyl Le$^x$ antigen was chosen for the production of the soluble leukosialin-IgG chimera. pcDNA-Fuc.TIII was constructed according to Kukowska-Latallo et al., supra. was kindly provided by Dr. John Lowe, Michigan University Medical Center.

C. PURIFICATION OF SOLUBLE CHIMERIC LEUKOSIALIN-IgG FROM CONDITIONED MEDIUM OF CHO CELLS

The CHO cell line expressing soluble chimeric leukosialin protein was cultured in A-MEM supplemented with 10% fetal calf serum, 0.5 µM methotrexate, and the medium was replaced with Opti-MEM (Bethesda Research Laboratories) after the cells reached confluence. After culturing for an additional 3 days, the conditioned medium (30 ml) was collected and directly applied to a column (1 ml) of Affi-Gel-protein A (Bio-Rad). The column was equilibrated with phosphate-buffered saline and washed with the same buffer. The bound protein was then eluted with 0.1 M glycine-HCl buffer, pH 3.8, and the eluted fractions (1 ml) were immediately neutralized with 225 µl of 1.5 M Tris, pH 8.8.

The fractions containing the chimeric protein, as assessed by immunoblotting with anti-human IgG-peroxidase conjugate, were concentrated by membrane filtration, and the concentrated sample was washed three times with phosphate-buffered saline by pressure dialysis. The solution obtained was then diluted with an equal volume of A-MEM with Hank's salts containing 5% fetal calf serum.

The detection of leukosialin by Western blotting was carried out exactly as described (Sawada et al., supra), using anti-leukosialin antibody (Leu-22, Becton Dickinson) and anti-mouse IgG-alkaline-phosphatase conjugate (Sigma).

In summary, the soluble leukosialin was prepared from CHO cells transfected with a vector that directs the expression of a soluble form of leukosialin and with a vector encoding Fuc-TIII. The transfected cells were confirmed to express sialyl Le$^x$ determinants by immunofluorescence as described (Williams and Fukuda, J. Cell Biol. 111:955–966 (1990)). In order to efficiently purify the soluble leukosialin, the cDNA sequence for leukosialin was fused with the sequence for the IgG constant and hinge region. The resultant protein was then purified by applying the conditioned cell medium to Affi-Gel-protein A, which is shown in FIG. 1.

The bound and subsequently eluted material from protein A was mostly composed of the desired chimeric protein ($M_r$~120,000) which reacted in Western blotting with anti-leukosialin antibodies. A soluble leukosialin IgG chimeric protein lacking the sialyl-Le$^x$ determinant was purified in a similar manner, except that a control CHO cell line used was stably transfected with the vector encoding the soluble leukosialin chimeric protein. This purified control protein also reacted with anti-leukosialin antibodies (FIG. 1B). These chimeric proteins behave as dimers in intact molecules since they contain interdisulfide bonds in the IgG hinge region (FIG. 1, A and B, lanes 5 and 6). In addition to the chimeric protein, two additional proteins were present as minor components. One of them migrated at the same position as bovine serum albumin ($M_r$~68,000), while the others appear to be a proteolytically processed material of the chimeric protein since it was reacted with anti-leukosialin antibodies. The latter also behaved as a dimer when analyzed without reduction (FIG. 1, A and B, lanes 5 and 6).

EXAMPLE II

Adhesion Assays: Methods and Materials

Adhesion of SP, C, L and SM cells to human umbilical vein endothelial cells, hereinafter, HUVEC (Clonetics, San Diego, Calif.), and CHO cells expressing E-selectin was carried out exactly as described in Sawada et al. J. Biol. Chem. 268:12675–12681 (1993).

The mouse endothelioma cell lines, eEnd.2, sEnd.1, tEnd.1, and bEnd.4 were kindly provided by Dr. R. Lindsay Williams at the Ludwig Institute for Cancer Research, victoria, Austria. These cell lines, originally derived from a subcutaneous (sEnd.1), thymic (tEnd.1), embryonal (eEnd.2), and brain (bEnd.4) hemangliomas produced in transgenic mice expressing polyoma middle T antigen (Williams et al., Cell 52:121–131 (1988)). The cells were maintained in Dulbecco's modified Eagle's medium containing 10% fetal calf serum. Mouse endothelioma cell lines were cultured in 96-well tissue culture plates and activated with 10 units/ml IL-1β (Sigma) and then washed with Dulbecco's modified Eagle's medium containing 5% fetal calf serum before the colonic carcinoma cells were added. As the control, non-activated mouse endothelial cells were prepared identically and used in parallel for the adhesion assays. The adhesion and inhibition of the adhesion by soluble lamp-1 and soluble leukosialin were carried out exactly as described previously (Sawada et al., supra).

Production of Sialyl Le$^x$ Glycolipid

Inhibition by sialyl Le$^x$-positive glycolipid, NeuNAcα2→3Galβ1→4-(Fucα1→3)GlcNAcβ1→3Galβ1→4Glc→Cer was tested after the glycolipid was incorporated into liposomes (Phillips et al., Science 250:1130–1132 (1990)). Paragloboside, NeuNAcα2→3Galβ1→4GlcNAcβ1→3Galβ1→4Glc→Cer was used as a control glycolipid. Sialyl Le$^x$ glycolipid (Kameyama et al., Carbohydr. Res. 209:C1–C4 (1991)) and paragloboside were kindly provided by Drs. Akira Hasegana, Gifu University, Japan, and Michiko Fukuda at this institute, respectively. In order to determine if sialyl Le$^x$ structure on the human colonic cells are recognized by mouse endothelial cells, the adhesion was assayed after the colonic cells were preincubated with anti-sialyl Le$^x$ antibody (CSLEX, IgM) or mouse anti-Le$^x$ monoclonal antibody (anti-PMN-6, IgM). The anti-PMN-6 antibody (Ball and Fanger, Blood 61:456–463 (1983)) was kindly provided by Dr. Ball of the Dartmouth Medical School.

Production of Soluble Lamp-1

SP cells were transfected with pcD-SRα encoding human lamp-1$^H$ cDNA as described (Sawada et al., supra). This cDNA encodes lamp-1 molecule of which cytoplasmic tyrosine was mutated into histidine. As shown previously (Williams and Fukuda, J. Cell Biol. 111:955–966 (1990)), the cytoplasmic tyrosine is critical for lysosomal targeting of lamp molecules and those with mutation at the cytoplasmic tyrosine are preferentially transported to the plasma membrane by the default pathway. The resultant SP transfectant, SP-pSR lamp-1$^H$, expressed three times more of cell surface lamp-1 than the parent SP cells (Sawada et al., supra).

Soluble lamp-1 was generated from CHO cells transfected with pSRαs-lamp-1 and purified from their culture supernatants as described (Sawada et al., supra). CHO cells were transfected with pcDL-SRα-478 encoding E-selectin and CHO cells expressing E-selectin were established as described (Sawada et al., supra).

EXAMPLE III

Adhesion of Colonic Carcinoma Cells to Human Umbilical Vein Endothelial Cells

Four cell lines with different metastatic potentials were used for these adhesion studies. The four human colonic carcinoma cell lines are KM12-C, KM12-SP, KM12-SM, and KM12-L4, (hereinafter C, SP, SM and L4), which are described in Saitoh et al.; J. Biol. Chem. 267:5700–5711 (1992), and Morikawa et al., Cancer Res. 48:1943–1948 (1988). The cell lines used in these experiments were provided by Dr. Isaiah J. Fidler M. D., of the Anderson Cancer Center, Houston, Tex. These sublines were established from one primary human colon carcinoma (Duke's stage B2), and were established as cell lines either as cells in culture or those grown after implantation of a human colonic carcinoma species in nude mice, as described in Morikawa et al.., supra (1988).

After intrasplenic injection, C and SP are poorly metastatic to liver, whereas SM and L4 are highly metastatic to liver (Morikawa et al., supra). The cell lines SP and L4 were obtained after implantation in spleen and those metastasized in the liver, respectively. The cell lines C and SM were derived from a similar implantation in cecum and its metastasized cells in the liver, respectively. As a positive control for adhesion, the low metastatic SP cell line was stably transfected with vector pSRαlamp-1$^H$. As shown previously, this cell line expresses an increased amount of lamp-1 on the cell surface and adheres strongly to activated human endothelium (Sawada et al., supra).

These four cell lines and the control SP-pSRαlamp-1$^H$ cell line were subjected to adhesion assays to determine their relative abilities to exhibit E-selectin-dependent adhesive properties.

Briefly, SP cells were metabolically labeled with [$^{35}$S]-methionine (100 μCi/ml, ICN) in methionine-free DME for 2 hours as described previously (Lee et al., J. Biol. Chem. 265:20476–20487 (1990)). The [$^{35}$S]-methionine labeled SP cells were harvested in the cell dissociation solution (Specialty Media, Lavellette, N.J.) and washed twice with DME before assay of the binding to HUVEC. HUVEC monolayers cultured in 96-well tissue culture plates, were activated with 5 unit/ml of IL-1β (Boehringer-Mannheim, Indianapolis, Ind.) for 4 hours and then washed with DME containing 5% fetal calf serum. Control non-activated HUVEC monolayers were prepared identically (without II-1β), and used in parallel for adhesion assays.

Figure 2:
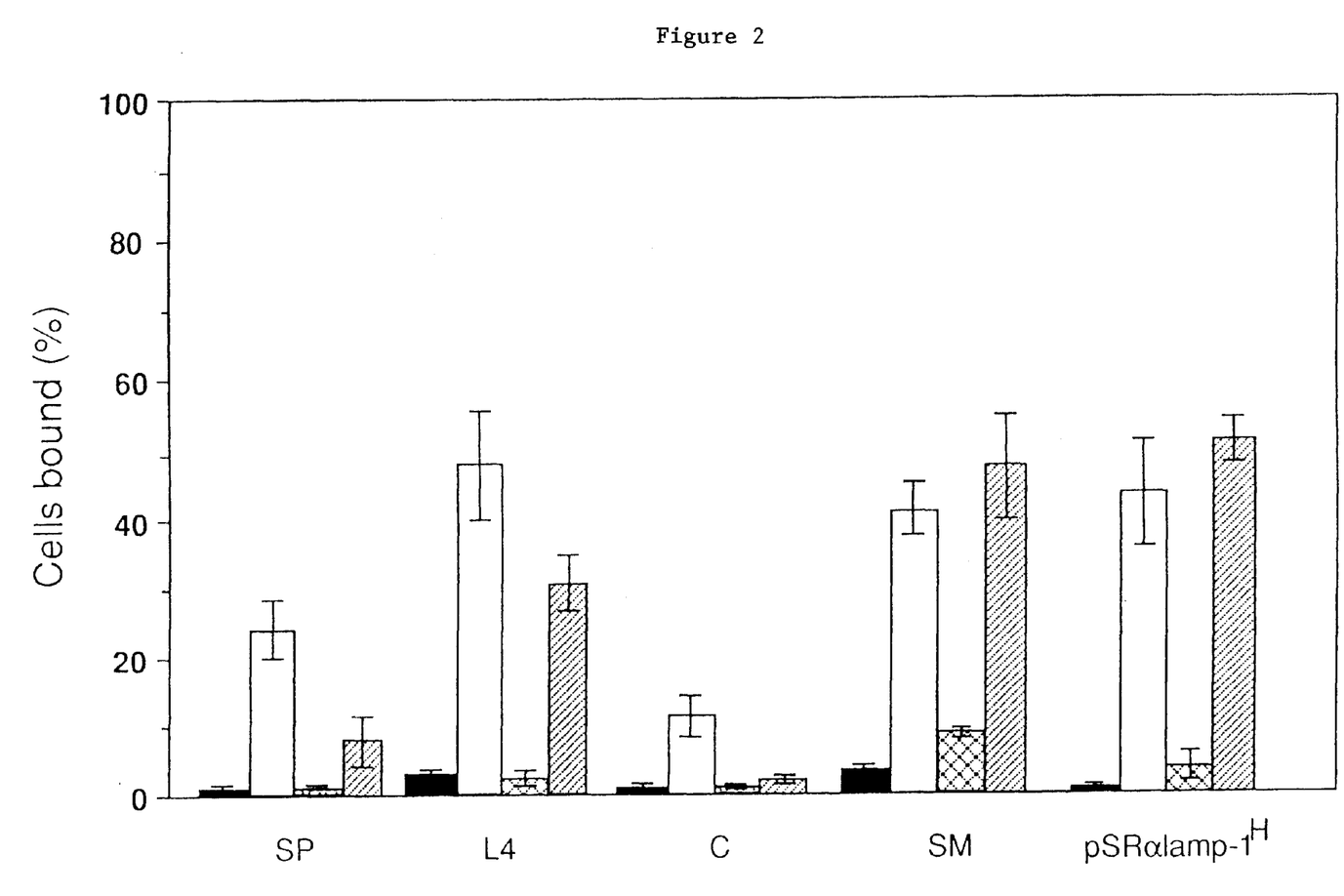
FIG. 2 shows the adhesion of various colonic carcinoma cells to human endothelial cells or E-selectin expressing CHO cells.

As shown in FIG. 2, a substantial fraction of the high metastatic L4 and SM cells as well as SP-pSRαlamp-$^H$ adhered to HUVEC monolayers, which were induced to express E-selectin by IL-1β. The same cells, on the other hand, were not bound detectably to the non-activated HUVEC.

The low metastatic SP and C cells adhered only modestly to activated HUVEC monolayers (FIG. 2). In FIG. 2, adhesion to IL-1β activated HUVEC monolayers is indicated by the open bars, whereas adhesion to non-activated HUVEC is represented by the solid bars. Adhesion to E-selectin-expressing CHO cell monolayers is denoted by hatched bars, and cross-hatched bars depict adhesion to control CHO monolayers. Data shown corresponds to the fraction of applied cells that remain after washing and represents the mean and standard deviation from four replicate assays.

Similar results were obtained when instead of activated HUVEC, CHO cells stably expressing E-selectin were tested. The high metastatic sublines L4 and SM bound strongly to the E-selectin-expressing CHO monolayers, but not to control CHO monolayers (FIG. 2). The low metastatic SP and C cells bound only moderately to the CHO monolayers expressing E-selectin.

These results indicate that, in this static assay, the efficiency of E-selectin-dependent adhesion correlates with the metastatic potential of the cells. As shown previously, the high metastatic sublines L4 and SM express more cell surface lamp-1 and lamp-2 molecules compared to the low metastatic SP and C sublines (Saitoh et al., J. Biol. Chem. 267:5700–5711 (1992)). In addition, it was shown that the high metastatic sublines express relatively more sialyl Le$^x$ determinants on the cell surface (Saitoh et al., supra). These combined results strongly suggest that the stronger adhesion to endothelial cells is one of the critical factors for tumor cells to be highly metastatic. The stronger adhesion is caused by an increased expression of sialyl Le$^x$ structures.

EXAMPLE IV

Adhesion of Different Colonic Carcinoma Cells to Mouse Endothelial Cells

Human and mouse E-selectins are highly homologous in their amino acid sequences (Weller et al., J. Biol. Chem. 267:15167–15183 (1992)). In order to demonstrate that mouse E-selectin also binds to cell surface sialyl Le$^x$ structures, the following experiments were performed.

Williams et al. supra established several mouse endothelioma cell lines from different origins: skin-derived endothelial cells (sEnd.1), thymus-derived endothelial cells (tEnd.1), embryonic endothelial cells (eEndo.2), and brain-derived endothelial cells (bEnd.4), as described in the Example above. It was shown recently that these cells have retained the functional properties of the original endothelium since they produce various cytokines upon stimulation as normal endothelial cells (Bussolino et al., J. Biol. Chem. 147:2122–2129 (1991)). Moreover, cDNA libraries from these cell lines were used to clone mouse E- and P-selectin (Weller et al., J. Biol. Chem. 267:15167–1518.3 (1992)). Therefore, these endothelioma cell lines were used as a model system for mouse endothelium since it is difficult to obtain a reasonable amount of normal endothelial cells from mouse.

Figure 3:
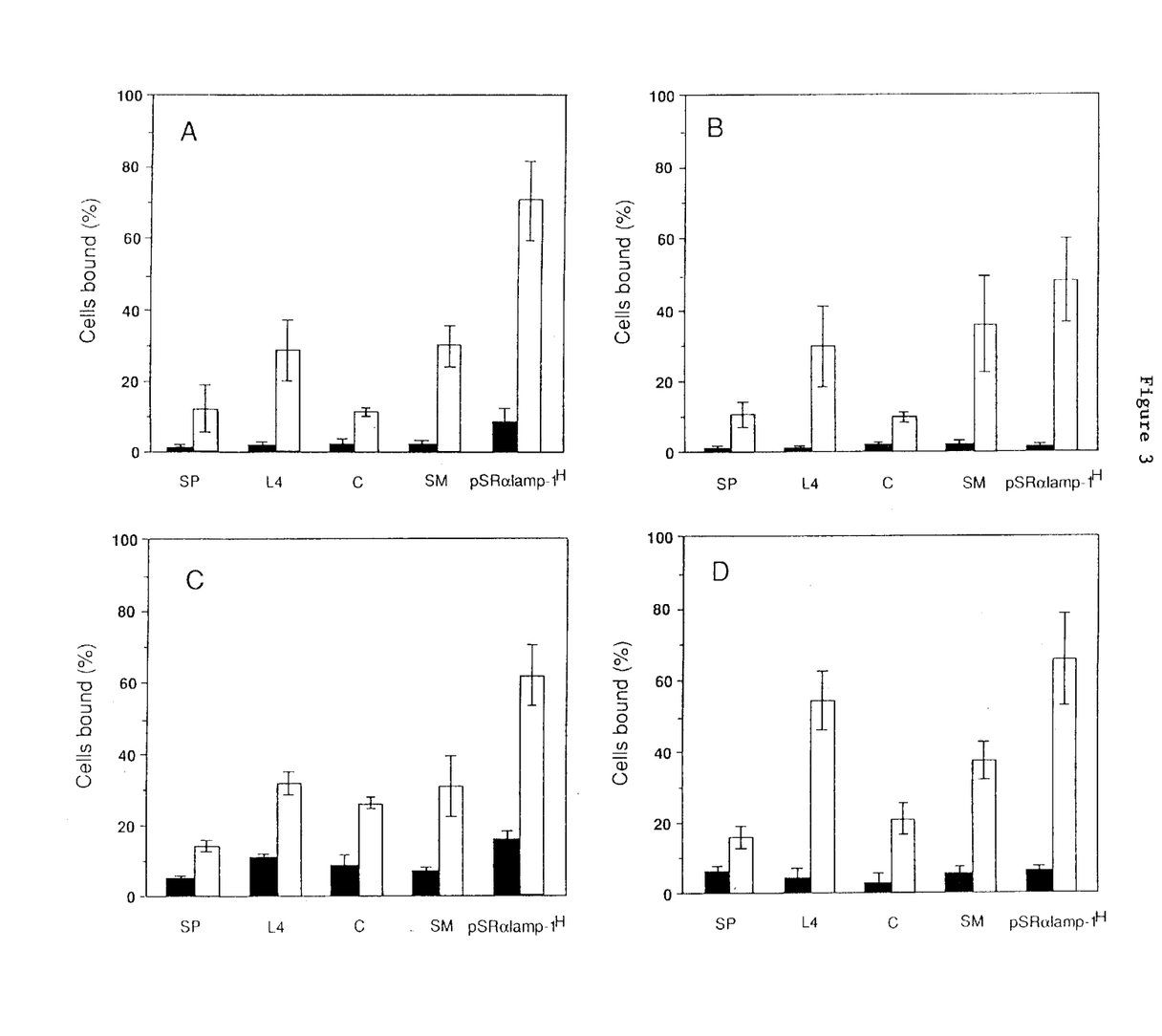

FIG. 3 illustrates the results obtained for the adhesion of the human colonic carcinoma cells used in Example III (and FIG. 2) to these different mouse endothelioma cells, where FIG. 3A shows adhesion to brain-derived endothelial cells (bEnd.4), FIG. 3B shows adhesion to mid gestation chimeric embryos (Endo.2), FIG. 3C shows adhesion to skin-derived endothelial cells (sEnd.1), and FIG. 3D shows adhesion to thymus-derived endothelial cells (tEnd.1). Adhesion to IL-1β-activated mouse endothelial monolayers is indicated by the open bars, whereas adhesion to non-activated mouse endothelial cells is represented by the solid bars. Data shown in FIG. 4 correspond to the fraction of applied cells that remained after washing, and represent the mean and standard deviation derived from four replicate assays.

The results indicate that these endothelioma cell lines do not express the necessary adhesion molecules without activation by IL-1β since the colonic cells hardly adhered to them before activation (see the closed bars). However, appreciable amounts of the carcinoma cells were bound to endothelioma cells after activation by IL-1β (see the open bars). When the adhesion efficiency was compared between the two sets of colonic carcinoma cells with different metastatic capability, SP and L4 cells showed the most striking difference. Nevertheless, regardless of the cell system, the high metastatic colonic carcinoma cells (L4 and SM) always adhered more strongly than the low etastatic ones (SP and C). This difference was most prominent for the adhesion to the brain, embryonic, and thymus endothelial cells (FIG. 3, A, B, and D).

On the other hand, such a difference was not so obvious for the adhesion to skin endothelioma cells (FIG. 3C), although low metastatic cells (SP and C) hardly bound to non-activated cells. It is not clear if this property of skin endothelioma cells reflects the property of normal skin endothelial cells or is deviated from normal cells because of its transformed nature.

As mentioned above, appreciably more SM and L4 cells were bound to human HUVEC or CHO cells expressing E-selectin than SP and C cells. These results taken together indicate that the difference in adhesion capability of these colonic carcinoma cells was the same regardless whether human HUVEC, E-selectin-expressing CHO cells, or mouse endothelial cell lines were used, suggesting strongly that the adhesion of colonic cells to activated mouse endothelial cells is most likely mediated through mouse E-selectin.

EXAMPLE V

Inhibition of E-selectin-Mediated Binding with Soluble Lamp-1 and Soluble Leukosialin In order to test if adhesion of colonic cells to activated mouse endothelial cells is mediated by sialyl $Le^x$ structures on the colonic cells, four independent experiments were carried out.

First, the binding of the cell line with the highest adhesion efficiency was tested in the presence of a sialyl $Le^x$ containing glycolipid. SM cells were subjected to adhesion to activated mouse tEnd.1 cells as described in Example IV (and FIG. 3) (open bar), or as in FIG. 3 after pretreatment of the activated monolayers with liposomes containing sialyl $Le^x$ glycolipid (hatched bars), or after pretreatment with liposomes containing the control glycolipid paragloboside (cross-hatched bar). The amount of glycolipid is shown in μg/ml at the x axis. The adhesion to non-activated mouse endothelial cells is shown by the closed bar. Data correspond to the fraction of applied cells still adherent to tEnd.1 cells after washing and are mean and standard deviation from four replicate assays.

As shown in FIG. 4, the adhesion of SM cells to tEnd.1 was inhibited by liposomes containing sialyl $Le^x$ glycolipid in a dose-dependent manner. In contrast, control liposomes containing sialyl paragloboside, which lacks sialyl $Le^x$ structures, did not inhibit the adhesion even at high concentrations.

Soluble lamp-1 and soluble leukosialin were tested for the ability to inhibit the adhesion of SM cells to mouse tEnd.1 cells. Sawada et al., supra describes the preparation of a soluble lamp-1 molecule containing the sialyl-$Le^x$ moiety. CHO cells were stably co-transfected with a vector that directs the expression of a soluble form of lamp-1 and the Fuc-TIII vector that encodes a human α-1,3/4-fucosyltransferase (as described in Weston et al., *J. Biol. Chem.* 267:24575–24584 (1992)), capable of creating the sialyl-$Le^x$ determinant using CHO cell oligosaccharide precursors (Lowe et al., *Cell* 63:475–484 (1990). As described in Sawada et al., supra (1993), soluble lamp-1 molecules containing the sialyl-$Le^x$ moiety and found that it inhibited the binding of the SP-pSRαlamp-$1^H$ to HUVEC. This soluble lamp-1 containing the sialyl $Le^x$ was also able to inhibit the adhesion of SM cells to activated mouse tEnd.1 cells in a dose-dependent manner (FIG. 5A).

The adhesion of SM cells to activated mouse tEnd.1 cells was tested for inhibition by soluble lamp-1 (FIG. 5A) or soluble leukosialin (FIG. 5B). The inhibition by soluble lamp-1 or soluble leukosialin derived from sialyl $Le^x$ positive CHO cells is shown by hatched bars.

Inhibition by control soluble lamp-1 or control soluble leukosialin, which were derived from sialyl $Le^x$ negative CHO cells, is shown by cross-hatched bars. The open bar represents the control without the inhibitors while the closed bar represents the adhesion to unstimulated mouse tEnd.1 monolayers. The experiments shown in FIGS. 5A and 5B were carried out at the same time.

FIG. 5C shows the adhesion of L4 cells to activated mouse tEnd.1 cells after L4 cells were preincubated with anti-sialyl $Le^x$ antibody (hatched bars) or anti-$Le^x$ antibody (cross-hatched bars). One standard deviation is indicated at the top of each bar. The amount of soluble lamp-1, soluble leukosialin and anti-sialyl $Le^x$ antibody is expressed as μg/50 μl on the x axis.

When these soluble leukosialin samples were tested in the adhesion assay, the purified sialyl-$Le^x$-positive leukosialin inhibited the adhesion of SM cells to mouse tEnd.1 cells in a concentration-dependent manner (FIG. 5B, hatched bars). In contrast, the control, sialyl-$Le^x$-negative leukosialin molecule inhibited the binding minimally, even at a concentration that for the sialyl $Le^x$-positive protein diminished binding to 30% of control levels (FIG. 5B, cross-hatched bar).

Finally, preincubation of the human colonic cells with anti-sialyl $Le^x$ antibody abolishes the binding to tEndo.1 cells. As shown in FIG. 5C, anti-sialyl $Le^x$ antibody inhibited the binding of L4 cells to tEndo.1 cells in a dose-dependent manner (hatched bars). In contrast, anti-$Le^x$ antibody did not inhibit the adhesion (cross-hatched bar).

These results suggest that binding of the human colonic carcinoma cells to mouse-activated endothelial cells are due to the binding of sialyl $Le^x$ structures on the human colon cells to adhesive molecules, most likely E-selectin on activated mouse endothelial cells. Second, it was shown that the sialyl-$Le^x$ determinant in the soluble lamp-1 or soluble leukosialin glycoproteins achieves a conformation which is recognized by E-selectin with an affinity sufficient to compete with the cell surface sialyl-$Le^x$ determinants that mediate adhesion to this selectin. These results indicate that soluble lamp-1 or soluble leukosialin are useful as therapeutic agents that block selectin-dependent inflammation or tumor metastasis.

Although this invention has been described with reference to the presently preferred embodiments, it is understood that various modifications can be made without departing from the spirit of the invention. Accordingly, the invention is limited only by the following claims.

We claim:

1. An antagonist to E-selectin mediated cell adhesion comprising a soluble chimeric leukosialin-IgG protein containing sialyl Le$^x$-termini in an amount sufficient to bind E-selectin.

2. The antagonist of claim 1, wherein said soluble chimeric leukosialin-IgG protein is soluble chimeric human leukosialin-IgG protein.

3. A composition containing the antagonist of claim 1 in addition to a carrier.

\* \* \* \* \*